(12) United States Patent
Nishikawa et al.

(10) Patent No.: US 8,563,802 B2
(45) Date of Patent: Oct. 22, 2013

(54) ABSORBENT ARTICLE WITH PATTERN

(75) Inventors: Kumiko Nishikawa, Kanonji (JP); Yuki Noda, Kanonji (JP); Kenichiro Kuroda, Kanonji (JP)

(73) Assignee: Unicharm Corporation, Ehime (JP)

( * ) Notice: Subject to any disclaimer, the term of this patent is extended or adjusted under 35 U.S.C. 154(b) by 447 days.

(21) Appl. No.: 12/919,953

(22) PCT Filed: Feb. 25, 2009

(86) PCT No.: PCT/JP2009/053996
§ 371 (c)(1),
(2), (4) Date: Nov. 8, 2010

(87) PCT Pub. No.: WO2009/110482
PCT Pub. Date: Sep. 11, 2009

(65) Prior Publication Data
US 2011/0046592 A1   Feb. 24, 2011

(30) Foreign Application Priority Data

Mar. 4, 2008 (JP) ................................ 2008-053807

(51) Int. Cl.
*A61F 13/15* (2006.01)
(52) U.S. Cl.
USPC ..................... 604/361; 604/385.04
(58) Field of Classification Search
USPC ........................... 604/361, 385.04
See application file for complete search history.

(56) References Cited

U.S. PATENT DOCUMENTS 4,623,340 A * 11/1986 Luceri ...................... 604/385.05
5,897,541 A * 4/1999 Uitenbroek et al. .......... 604/358
6,117,523 A * 9/2000 Sugahara ..................... 428/134
6,719,742 B1 * 4/2004 McCormack et al. ... 604/385.01
7,432,412 B2 10/2008 Kigata et al.
(Continued)

FOREIGN PATENT DOCUMENTS

EP    0951889 A1   10/1999
JP    59190230 U   12/1984
(Continued)

OTHER PUBLICATIONS

ISR for PCT/JP2009/053996 dated Jun. 9, 2009.
(Continued)

*Primary Examiner* — Lynne Anderson
(74) *Attorney, Agent, or Firm* — Lowe, Hauptman & Ham

(57) ABSTRACT

To apply a clear pattern to an absorbent article such as sanitary napkin without worsening the soft and comfortable touch to skin and allowing the colorant from coming into direct contact with the skin of a wearer.

An absorbent article comprising a liquid-permeable sheet, a liquid-impermeable sheet, an absorber sandwiched between the liquid-permeable sheet and the liquid-impermeable sheet, and side sheets joined to at least a part of the right and left both sides of the liquid-permeable sheet and to at least a part of the liquid-impermeable sheet, wherein a plurality of recess parts are provided in the side sheet, at least the portion provided with the recess part has a colored layer between the side sheet and the liquid-permeable sheet, and the recess part appears in a color different from the portion other than the recess part. The recess part is provided by stacking the liquid-permeable sheet, the colored layer and the side sheet in this order and applying embossing from the side sheet side to the region where the colored layer is present.

16 Claims, 7 Drawing Sheets

(56) References Cited

U.S. PATENT DOCUMENTS

| | | |
|---|---|---|
| 2002/0062115 A1 | 5/2002 | Wada et al. |
| 2003/0026945 A1 | 2/2003 | Lasko |
| 2004/0015145 A1* | 1/2004 | Miura et al. ............... 604/367 |
| 2006/0129115 A1 | 6/2006 | Visscher et al. |
| 2006/0142710 A1* | 6/2006 | Kigata et al. ............... 604/361 |

FOREIGN PATENT DOCUMENTS

| | | |
|---|---|---|
| JP | 63-99301 A | 4/1988 |
| JP | 6-21624 A | 3/1994 |
| JP | 6-142135 A | 5/1994 |
| JP | 2001140154 A | 5/2001 |
| JP | 2006-110225 A | 4/2006 |
| JP | 2006181192 A | 7/2006 |
| JP | 2007216031 A | 8/2007 |
| JP | 2007-330822 A | 12/2007 |
| WO | 2006/066028 | 6/2006 |

OTHER PUBLICATIONS

Supplementary European Search Report corresponding to EP 09718342, dated Mar. 22, 2012.

Japanese Office Action issued in Application No. 2008-053807, dated Apr. 23, 2013.

* cited by examiner

ABSORBENT ARTICLE WITH PATTERN

RELATED APPLICATIONS

The present application is National Phase of PCT/US2009/053996 filed Feb. 25, 2009, and claims priority from Japanese Application Number 2008-053807 filed Mar. 4, 2008.

TECHNICAL FIELD

The present invention relates to an absorbent article. More specifically, the present invention relates to an absorbent article, such as a sanitary napkin and diaper, where a pattern is applied.

BACKGROUND ART

An absorbent article having a side sheet subjected to design embossing is known (see Japanese Unexamined Patent Publication No. 2006-110225). The invention disclosed in Japanese Unexamined Patent Publication No. 2006-110225 is intended to efficiently produce an absorbent article without causing breakage of a sheet material, in which wrinkling or twisting does not readily occur, flexibility decreases less, touch to skin is good, stuffiness does not readily occur, an embossed part with high visibility is provided, and satisfactory leakage prevention is achieved. However, the embossed part disclosed in Japanese Unexamined Patent Publication No. 2006-110225 has the same color as that of the non-embossed part and visibility is not necessarily high.

An absorbent article having a side sheet in which a pattern is formed by printing is also known (see Japanese Unexamined Patent Publication No. 2006-181192). The invention disclosed in Japanese Unexamined Patent Publication No. 2006-181192 is intended to let a wearer know the presence of the side sheet by printing a pattern and providing a sense of security in terms of leakage prevention, and for keeping the printing ink from substantially contacting the skin of the wearer, a method of forming a recess part by an emboss roll and at the same time, transferring ink to the bottom of the recess part, a method of printing a pattern on the surface not in direct contact with the skin of the wearer, i.e., on the back surface of the side sheet, and a method of printing a pattern on the back surface sheet are disclosed.

DISCLOSURE OF INVENTION

According to the technique disclosed in Japanese Unexamined Patent Publication No. 2006-110225, even if design embossing could be applied in a uniform state, the part subjected to embossing is white and in turn, the embossed part is also white or nearly white, although the embossed part differs in light transmittance from the non-embossing part. Accordingly, when the wearer changes the absorbent article, the design cannot be easily seen in a dark place without light, such as inside of a toilet room. Also, the method which may be considered for clearly showing the embossing has a problem that this can be coped with only by production conditions such as heat, pressure and clearance, as a result, the embossed part becomes hard and gives an uncomfortable feeling when touching the skin, such as prickling and rubbing.

In the case of the method disclosed in Japanese Unexamined Patent Publication No. 2006-181192 where a recess part is formed by an emboss roll and at the same time, ink is transferred to the bottom of the recess part, the process is complicated and not practical, for example, there may be a possibility that ink bleeding may occur when forming the recess part and the ink attaches to the receiving roll and is transferred to a portion other than the recess part. The recess part may not be stably formed or the ink disposed in the recess part may transfer to the skin surface due to body pressure of the wearer. Furthermore, in the case of the method of printing a pattern on a surface not in direct contact with the skin of the wearer or printing a pattern on the back surface sheet, the pattern is visually recognized through the side sheet and this gives rise to a problem that the visibility of the pattern is not necessarily high.

The absorbent article of the present invention is an absorbent article comprising a liquid-permeable sheet, a liquid-impermeable sheet, an absorber sandwiched between the liquid-permeable sheet and the liquid-impermeable sheet, and side sheets joined to at least a part on the right and left both sides of the liquid-permeable sheet, wherein a plurality of recess parts are provided in the side sheet, at least the portion provided with the recess part has a colored layer between the side sheet and the liquid-permeable sheet, and the recess parts appear in a color different from the portion other than the recess parts.

In a preferred embodiment of the present invention, the recess parts are provided by embossing; the colored layer is provided in an overlapped portion of the side sheet with the liquid-permeable sheet; the light transmittance of the side sheet is 70% or less; the thickness of the side sheet is from 0.2 to 1.5 mm under a load of 3 g/cm$^2$; the colored layer comprises a hot-melt resin containing a colorant; and the colored layer contains from 0.1 to 10 parts by weight of a colorant based on 100 parts by weight of the hot-melt resin.

The method of the present invention is a method for producing an absorbent article which comprises a liquid-permeable sheet, a liquid-impermeable sheet, an absorber sandwiched between the liquid-permeable sheet and the liquid-impermeable sheet, side sheets joined to at least a part on the right and left both sides of the liquid-permeable sheet, and a colored layer provided between the liquid-permeable sheet and the side sheets, and is provided with a plurality of recess parts appearing in a color different from the portion other than the recess parts, the method comprising stacking a liquid-permeable sheet, a colored layer and a side sheet in this order and applying embossing from the side sheet side to the region where the colored layer is present, thereby providing a plurality of recess parts in the side sheets.

The absorbent article of the present invention has a recess part differing in the color and therefore, a pattern by the recess part is clearly visible. At the same time, a colored layer is disposed below a side sheet and this enables keeping the colored layer from coming into direct contact with the skin surface.

Embossing is applied to the side sheets and the colored layer which differ in color, and the recess part formed by the embossing causes the side sheets and the colored layer to come close and be press-bonded, so that in the recess part, the color of the colored layer can be easily recognized when viewed from the side sheet side. Furthermore, colored parts are provided on both sides of the product and therefore, the boundary of the absorbing surface with both sides is easily visible. As a result, for example, on changing the napkin, the replacement timing can be momentarily judged by the distance between the colored part and the range where menstrual blood has spread.

BEST MODE FOR CARRYING OUT THE INVENTION

Figure 1:
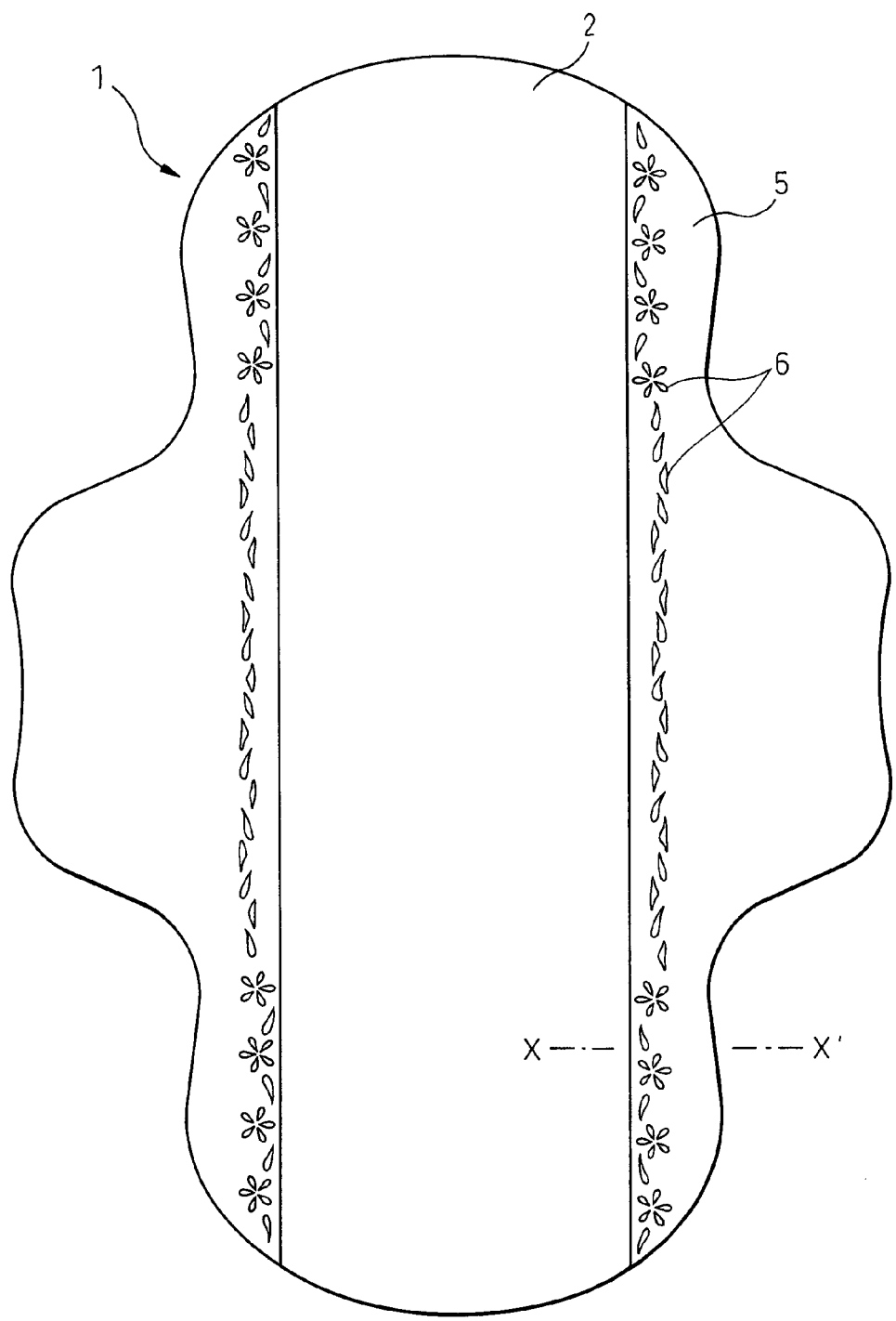
FIG. 1 is a plan view of one embodiment of the absorbent article of the present invention.

The present invention is described below by referring to the drawings, but the present invention is not limited to those illustrated in the drawings.

Figure 2:
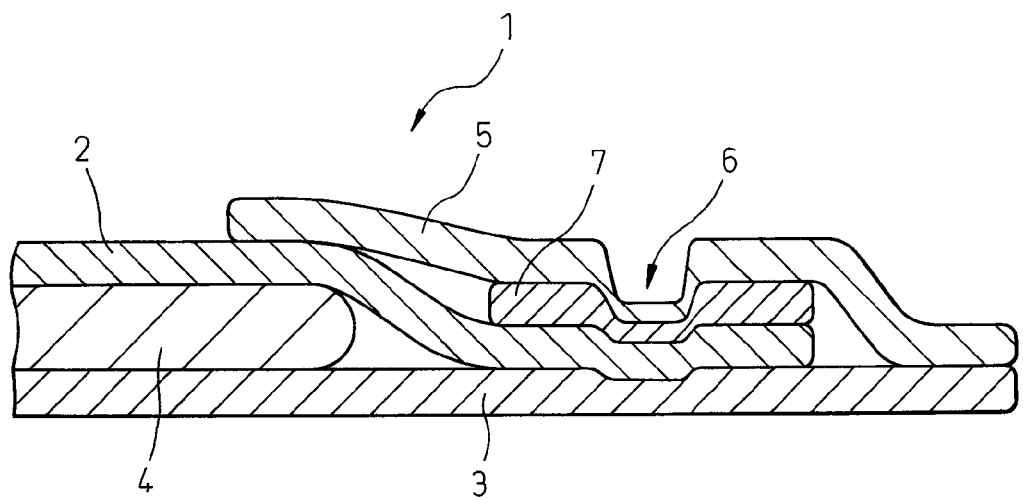
FIG. 2 is a cross-sectional view of one embodiment of the absorbent article of the present invention.

FIG. 1 is a plan view of one embodiment of the absorbent article of the present invention, and FIG. 2 is its X-X' cross-sectional view.

The absorbent article 1 of the present invention comprises a liquid-permeable sheet 2, a liquid-impermeable sheet 3, an absorber 4 and side sheets 5. The absorber 4 is sandwiched between the liquid-permeable sheet and the liquid-impermeable sheet. In the side sheets 5, a plurality of recess parts 6 are provided. Between the side sheet 5 and the liquid-permeable sheet 2, a colored layer 7 is provided at least in the portion where the recess part is provided. In the recess part, the side sheet 5 and the colored layer 7 are press-bonded and therefore, the recess part and the portion other than the recess part appear in different colors.

In the absorbent article of the present invention, a cushion layer (not illustrated) may be further provided between the liquid-permeable sheet 2 and the absorber 4. The liquid-permeable sheet and the absorber are, or the liquid-permeable sheet, the cushion layer and the absorber are joined, for example, by pin embossing.

The absorbent article of the present invention is preferably used as a sanitary napkin, a diaper or the like. In use as a sanitary napkin or a diaper, the absorbent article is worn such that the liquid-permeable sheet surface comes into contact with the skin of the wearer.

The absorbent article may have, for example, in the case of a sanitary napkin, a rectangular shape, an oval shape, a gourd shape, or a shape equipped with so-called wings for preventing slippage from the shorts and is not particularly limited in its shape as long as it fits to the women's body or the shape of shorts. The total outside dimension is preferably from 100 to 500 mm, more preferably from 150 to 350 mm, in the long direction and is preferably from 30 to 200 mm, more preferably from 40 to 180 mm, in the short direction.

The liquid-permeable sheet constituting the absorbent article of the present invention is used to exert a function of passing a liquid excretion from the body, such as menstrual blood and urine, down to the absorber provided as the underlying layer and at the same time, hold an absorber by sandwiching it between the liquid-permeable sheet and the liquid-impermeable sheet. The liquid-permeable sheet is entirely or partially liquid-permeable, and the liquid permeation area is formed of, for example, a resin film having formed therein a large number of openings for permeating liquid, a net-like sheet having a large number of meshes, or a liquid-permeable nonwoven or woven fabric. As for the resin film or net-like sheet, those formed from polypropylene (PP), polyethylene (PE), poly(ethylene terephthalate) (PET) or the like may be used. As to the nonwoven fabric, for example, a spunlaced nonwoven fabric formed from a cellulose fiber such as rayon, a synthetic resin fiber or the like, and an air-through nonwoven fabric formed from a synthetic resin fiber may be used. A biodegradable natural product, such as poly(lactic acid), chitosan or poly(alginic acid) may be used as the material. Furthermore, in combination with forming a large number of openings for permeating liquid, a silicone-containing or fluorine-containing water-repellent oily agent may be coated to deter attachment of a body fluid to the outer surface.

The basis weight of the liquid-permeable sheet is preferably from 15 to 100 g/m$^2$, more preferably from 20 to 50 g/m$^2$, still more preferably from 25 to 40 g/m$^2$. If the basis weight is less than 15 g/m$^2$, sufficient surface strength may not be obtained and the sheet may rupture during usage, whereas if the basis weight exceeds 100 g/m$^2$, excessive roughness develops and an uncomfortable feeling occurs during usage. Furthermore, in use for a long time, if the basis weight exceeds 40 g/m$^2$, the liquid is held in the liquid-permeable sheet and stays in a sticky state and this leads to discomfort. The density is not particularly limited as long as it is 0.12 g/cm$^3$ or less and the sheet is liquid-permeable. If the density exceeds this range, smooth permeation between fibers of the liquid-permeable sheet becomes difficult. In the case of menstrual blood, the viscosity is higher than urine or the like, and therefore the density is preferably low.

In the case where the liquid permeation area constituting the entirety or a part of the liquid-permeable sheet is a perforated film such as film having formed therein a large number of openings for permeating liquid, it is preferred that the opening diameter is from 0.05 to 3 mm, the pitch is from 0.2 to 10 mm, and the opening area percentage is from 3 to 30%.

In the absorbent article of the present invention, a second liquid-permeable sheet may be further provided between the liquid-permeable sheet and the absorber. For the second liquid-permeable sheet, a sheet formed of a material similar to the above-described liquid-permeable sheet (for example, nonwoven fabric) and having a density slightly higher than that of the above-described liquid-permeable sheet is used, and this sheet may be provided so as to accelerate the movement of liquid to the absorber or prevent the liquid from being released from the absorber.

The liquid-impermeable sheet constituting the absorbent article of the present invention has a function of preventing liquid such as menstrual blood and urine absorbed by the absorber from leaking outside, and a material capable of preventing outside leakage of such a liquid is used. When a material that does not pass a liquid, but having air permeability is used, stuffiness when wearing can be reduced and discomfort during wearing can be relieved. Examples of such a material include a liquid-impermeable film mainly comprising polyethylene (PE) or polypropylene (PP), an air-permeable film, and a composite sheet obtained by laminating a liquid-impermeable film on one surface of a nonwoven fabric such as spunbonded fabric. Preferably, a hydrophobic nonwoven fabric, a water-impermeable plastic film, a laminate sheet of nonwoven fabric with water-impermeable plastic film, or the like may be used. An SMS nonwoven fabric where a highly water-resistant melt-blown nonwoven fabric is sandwiched between high-strength spunbonded nonwoven fabrics may also be used.

The absorber constituting the absorbent article of the present invention has a function of absorbing and holding a liquid such as menstrual blood and urine, and a bulky material that does not readily lose shape and causes less chemical irritation, is preferred. Examples thereof include an absorber composed of a fluffed pulp or an air-laid nonwoven fabric and a super-absorbent polymer. Instead of a fluffed pulp, for example, a chemical pulp, a cellulose fiber and an artificial cellulose fiber such as rayon and acetate may be used. The absorber includes a mixture of a pulp having a basis weight of 500 g/m$^2$ and a polymer having a basis weight of 20 g/m$^2$ (the polymer is dispersed in the entirety), in which the pulp and the polymer are uniformly distributed over all and which is wrapped with a tissue having a basis weight of 15 g/m$^2$. Examples of the air-laid nonwoven fabric include a nonwoven fabric in which pulp and a synthetic fiber are thermally fused or bonded by a binder. The super-absorbent polymer (SAP) has a three-dimensional network structure in which a water-soluble polymer is appropriately crosslinked, and this polymer absorbs hundreds to thousands of times of water, but is substantially water-insoluble and does not release the once absorbed water even when pressure is applied. Examples thereof include starch-based, acrylic acid-based and amino acid-based particulate or fibrous polymers. The shape and structure of the absorber may be changed as needed, but the total liquid absorption amount of the absorber needs to cope with the designed insertion amount as an absorbent article and the desired usage. The size, absorption capacity and the like of the absorber are varied according to the usage.

Figure 3A:
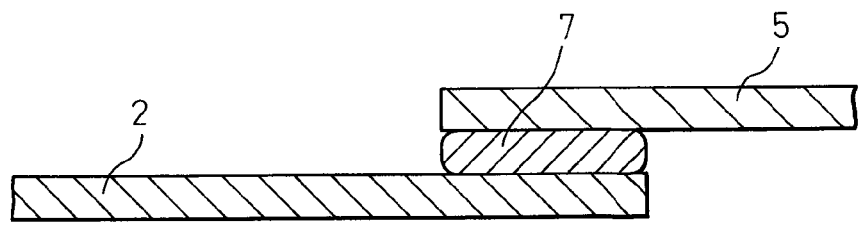
FIG. 3(a) is a cross-sectional view illustrating one example of various embodiments when joining the side sheet to the liquid-permeable sheet.
Figure 3B:
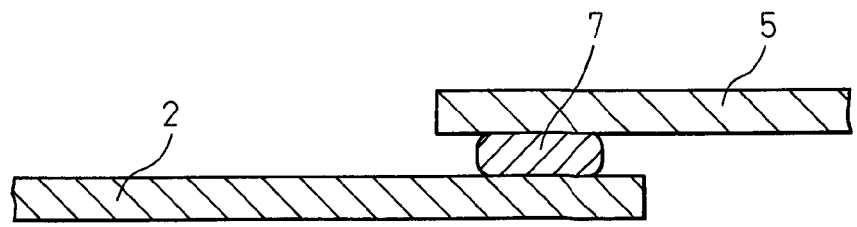
FIG. 3(b) is a cross-sectional view illustrating one example of various embodiments when joining the side sheet to the liquid-permeable sheet.
Figure 3C:
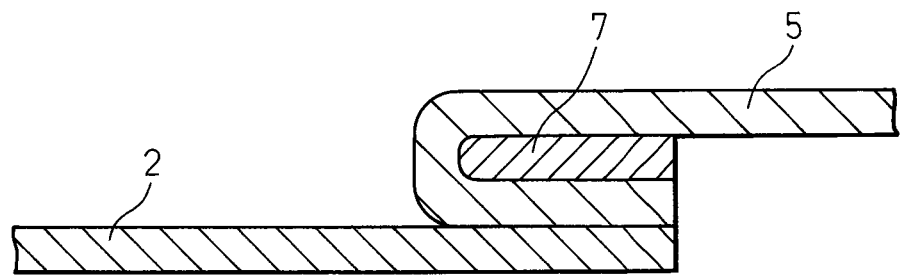
FIG. 3(c) is a cross-sectional view illustrating one example of various embodiments when joining the side sheet to the liquid-permeable sheet.
Figure 3D:
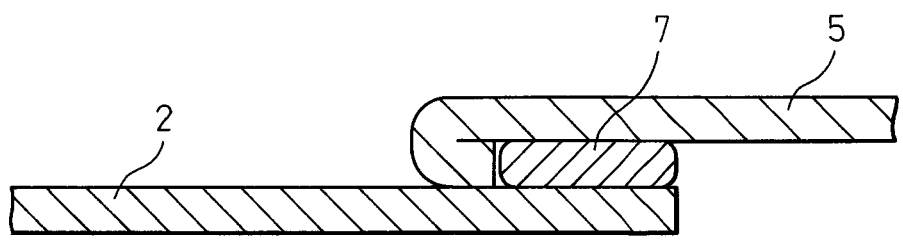
FIG. 3(d) is a cross-sectional view illustrating one example of various embodiments when joining the side sheet to the liquid-permeable sheet.
Figure 3E:
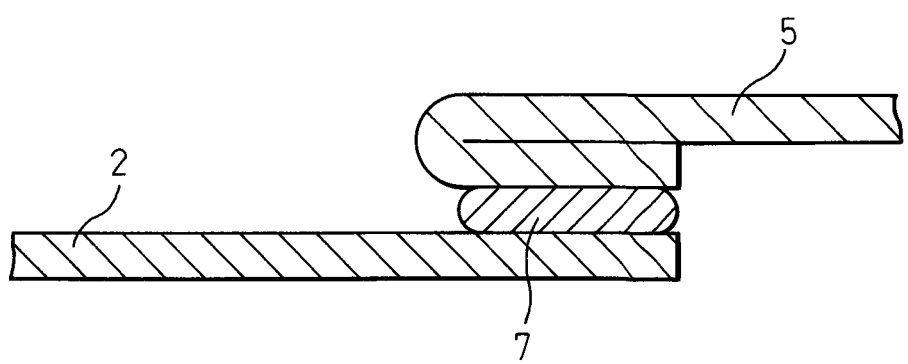
FIG. 3(e) is a cross-sectional view illustrating one example of various embodiments when joining the side sheet to the liquid-permeable sheet.

The side sheet 5 constituting the absorbent article of the present invention is joined to at least a part on both sides of the liquid-permeable sheet 2. The side sheet 5 may be further joined to at least a part of the liquid-impermeable sheet 3. In a typical embodiment, as illustrated in FIG. 1, the side sheets are provided on right and left both sides of the absorbent article, and the shape thereof is nearly the same as the liquid impermeable sheet in the overlapped portion with the liquid impermeable sheet. As illustrated in FIG. 2, the side sheet is partially overlapped with the lateral edge of the liquid-permeable sheet and in the portion not overlapped with the liquid-permeable sheet, is overlapped with the liquid-impermeable sheet and at least partially jointed thereto. The side sheet 5 is joined to the liquid-permeable sheet 2 and the liquid-impermeable sheet 3, for example, by a hot melt/heat embossing. Between the side sheet 5 and the liquid-permeable sheet 2, a colored layer is at least partially present, but other layers such as adhesive layer and turned-back portion of the side sheet may be further present. Also between the side sheet 5 and the liquid-impermeable sheet 3, other layers such as colored layer and adhesive layer may intervene. As illustrated in FIG. 2, FIG. 3(a) and FIG. 3(b), the side sheet may be laminated to the liquid-permeable sheet through a colored layer, or as illustrated in FIG. 3(c), the side sheet may be turned back to the liquid-permeable sheet side and a colored layer may be inserted in the folded portion. As illustrated in FIG. 3(d), a colored layer may not be inserted in the folded portion due to short folding width of the side sheet, or as illustrated in FIG. 3(e), a colored layer may be disposed below the fold of the side sheet. Furthermore, the side sheet may form stretchable gathers by using an elastic yarn. The side sheet may also be provided as a lamination seal for forming a pocket.

As for the material constituting the side sheet, an air-through nonwoven fabric, a spunbonded fabric, a film or a perforated film may be used, with an air-through nonwoven fabric being preferred.

If the light transmittance of the side sheet is too high, when a colored layer is present also in the portion not subjected to embossing, the color of the colored layer is seen through from the side sheet side and the recess part may not become distinguishable, despite appearing as a dark color. Accordingly, the light transmittance of the side sheet is preferably 70% or less, more preferably from 30 to 65%. The side sheet need not be white and may have a color other than white as long as the recess part can be visually recognized as different color-looking. The side sheet having a preferred light transmittance can be obtained, for example, by mixing a colorant in the side sheet. For example, in the case of decreasing the light transmittance of the white side sheet as it is, titanium oxide is used and the blending amount thereof is set to be from 0.1 to 50% by weight, preferably from 1 to 10% by weight, based on the entire fiber. The method for decreasing the light transmittance of the side sheet also includes a method of decreasing the diameter of the fiber constituting the nonwoven fabric. In this case, the appropriate size of the fiber is 6.6 dtex or less, preferably from 0.1 to 3.3 dtex.

As for the thickness (bulk) of the side sheet, when the side sheet is a nonwoven fabric, if the bulk is lost by embossing or the like, even a material having the same basis weight allows the color to be seen through the non-embossed part. The side sheet when compressed may be impregnated with a hot melt resin, and therefore the material used as the side sheet needs to have a certain degree of thickness/bulk. The thickness of the side sheet is preferably 0.2 mm or more, more preferably from 0.3 to 1.5 mm under a load of 3 g/cm$^2$.

A perforated nonwoven fabric material or a perforated film may also be used as the side sheet. In this case, three kinds of states are obtained, i.e., originally, the color of the colored layer is viewed directly from the openings and the color is seen through in the non-open parts, and when embossing is applied, the embossed part appears as a dark color. As a result, the open portions of the openings can also be looked like a pattern. The perforated sheet tends to be increased in bulk by the formation of a rib part, and as described above, this is effective in maintaining the liquid-permeable sheet at a distance from the colored layer. In the case of using a liquid-impermeable film mainly comprising polyethylene, polypropylene or the like, the light transmittance of the film itself is low, but the thickness is small. However, by adhering a rolled-up and wrinkled film to the colored layer or applying a gearing process so as to maintain the liquid-permeable sheet at a distance from the colored layer, seeing the color of the colored layer through the non-recess part can be reduced.

The colored layer constituting the absorbent article of the present invention needs to be disposed at least in the portion where a recess part is provided, but the range in which the colored layer is disposed may be the whole or a part of the side sheet, or the colored layer may be disposed to create gradation.

The colored layer needs to be in a color different from that of the side sheet. This color is selected by taking into consideration the psychological effect but may be any color. The material constituting the colored layer is not particularly limited as long as it is a colored material such as an ink, a coloring material, a resin containing a colorant (a colored resin), a nonwoven fabric having kneaded therein a colorant or a nonwoven fabric having coated on the surface thereof a colorant (a colored nonwoven fabric), or a film having kneaded therein a colorant or a film having coated on the surface thereof a colorant (a colored film), but the material is preferably a hot-melt resin containing a colorant, an adhesive containing a colorant or a hot-melt adhesive containing a colorant, more preferably a hot-melt adhesive containing a colorant. A material obtained by forming a colorant-containing hot-melt resin into a film or sheet may also be used as the colored layer. In the case where a colorant-containing hot-melt resin is used as the colored layer, when heat embossing is applied from the side sheet side, the hot-melt resin constituting the colored layer is melted due to heat applied during press-bonding and allowed to penetrate into and be fixed on the side sheet side and therefore, the embossed part appears in a dark color as compared with its peripheral site. In the case where a colored nonwoven fabric or a colored film is used as the colored layer, unlike the case of using a colorant-containing hot-melt resin, it does not occur that a hot-melt resin is melted due to heat and allowed to penetrate into and be fixed on the side sheet, but when embossing is applied and the side sheet having a certain degree of thickness is thereby joined to the colored layer, the side sheet comes close to the colored layer in the recess part and is fixed, and therefore the color tone of the colored layer becomes easily visible when viewed from the side sheet side of the recess part, as compared with the non-recess part. In order to maintain the press-bonded state of the side sheet to the colored layer, a hot-melt resin may be coated therebetween. The colored nonwoven fabric can be obtained, for example, by previously kneading a colorant composed of a pigment or the like into a resin constituting a synthetic fiber, spinning a fiber from the resin to obtain a colored fiber, and processing the fiber into a nonwoven fabric. The colored film can be obtained, similarly, by previously kneading a colorant composed of a pigment or the like into a resin constituting a film and forming the resin into a sheet.

As for the colorant, a dye and a pigment both may be used. Examples of the dye include a direct dye typified by C.I. Direct Blue or the like, a reactive dye typified by C.I. Reactive Blue or the like, and an acid dye typified by Blue No. 1 or the like. As for the pigment, either an inorganic pigment or an organic pigment may be used, and examples of the organic pigment include Red No. 404.

In the case where the colored layer is a colorant-containing hot-melt resin, the content of the colorant is preferably 0.1 parts by weight or more, more preferably from 0.1 to 10 parts by weight, based on 100 parts by weight of the hot-melt resin. If the content of the colorant is too small, the color of the recess part is light and the pattern becomes unclear, whereas if the content of the colorant is excessively large, the color in the portion other than the recess part also becomes dark and the pattern becomes unclear.

In the case where the light transmittance of the side sheet is high, the color of the colored layer is seen through the portion other than the recess part. When the mixing ratio of the colorant in the colored layer is low, the color tone of the recess part is not so different from that in the periphery thereof and the original purpose cannot be achieved. The matter of importance is the difference in color tone (color difference) between the recess part and the non-recess part. The range of the color difference between the non-recess part and the recess part, in which a difference in the color tone can be perceived, is $\Delta E=6$ or more, preferably from $\Delta E=6$ to $\Delta E=10$. Incidentally, as for the color difference, a color difference base of a combination of the side sheet and the colored layer is measured using a colorimeter (manufactured by Minolta Co., Ltd.) and after removing the side sheet, only the colored layer is measured, whereby the color difference value $\Delta E$ can be measured. Describing $\Delta E$ indicative of the color difference, the $L^*a^*b^*$ color system is a color system standardized by International Commission on Illumination (CIE) in 1976, which is widely used at present in various fields for indicating the color of a thing. In the $L^*a^*b^*$ color system, the brightness is represented by $L^*$, and the chromaticity indicating hue and chroma is represented by $a^*$ and $b^*$. The direction of color is shown, for example, $a^*$ is red direction, $-a^*$ is green direction, $b^*$ is yellow direction and $-b^*$ is blue direction. As the numerical value increases, the color becomes brighter. In the case of $L^*a^*b^*$ color system, the color difference can be indicated by the numerical value of $\Delta E^*ab$, and a color difference of two colors can be indicated by one numerical value. The calculation formula is $\Delta E^*ab=[(\Delta L^*)2+(\Delta a^*)2+(\Delta b^*)2]^{1/2}$.

With respect to the colored layer, when importance is attached to how it looks by a color difference, the side sheet may be white but need not be white. For example, also by using a color opposite the color of the colored layer in terms of hue for the side sheet, the above-described contrast can be made large. Furthermore, by using such different colors, these two colors are mixed in the recess part and a third color is formed. For example, when the side sheet is red and the colored layer is blue, the recess part is colored violet.

The absorbent article of the present invention can be produced by stacking a liquid-permeable sheet, a colored layer and a side sheet in this order and applying embossing from the side sheet side to the region where the colored layer is present, thereby providing a plurality of recess parts in the side sheet. A liquid-impermeable sheet and an absorber may be stacked on the liquid-permeable sheet, colored layer and side sheet before applying embossing or may be stacked on the liquid-permeable sheet, colored layer and side sheet after applying embossing.

The colored layer may be previously provided at least in a portion of the side sheet, where a recess part is intended to be provided. In this case, the side sheet provided with the colored layer is stacked on the liquid-permeable sheet such that the side sheet surface having provided thereon the colored layer faces the liquid-permeable sheet, and embossing is applied from the side sheet side to the region where the colored layer is present.

The colored layer may also be previously provided at least in a portion of the liquid-permeable sheet, where a recess part is intended to be provided. In this case, the side sheet is stacked on the liquid-permeable sheet surface having provided thereon the colored layer, and embossing is applied from the side sheet side to the region where the colored layer is provided.

After preparing a two-layer sheet where the side sheet and the colored layer are previously stacked, the two-layer sheet may be stacked on the liquid-permeable sheet such that the surface on the colored layer side faces the liquid-permeable sheet, and embossing may be applied from the side sheet side.

Furthermore, after applying embossing to the side sheet to form a recess part, the colored layer may be disposed on the back surface of the side sheet, and the liquid-permeable sheet, absorber and liquid-impermeable sheet may be disposed therebelow. In this case, the portion of the recess part provided in the side sheet becomes thinner than the portion other than the recess part to make more see-through the colored layer disposed therebelow and therefore, the recess part appears in a color different from the portion other than the recess part.

Preferably, a colorant-containing hot-melt resin is used as the colored layer, the colored layer is previously coated at least on a portion of the side sheet where a recess part is intended to be provided, the liquid-permeable sheet is stacked in sequence, the side sheet coated with the colored layer is stacked on the liquid-permeable sheet such that the side sheet surface provided with the colored layer faces the liquid-permeable sheet, and embossing is applied from the side sheet side to the region where the colored layer is present.

In the case of using a colorant-containing hot-metal resin, a new design can be created by the combination of the coating pattern of the hot-melt resin and the design embossing. Examples of the method for coating a colorant-containing hot-melt resin on the side sheet include solid pattern forming (no omission) by a slot coater, pattern forming with omission (striped) by a slot coater, control seam coating (wavy), spiral coating, and design coating by a roll coater.

Figure 4A:
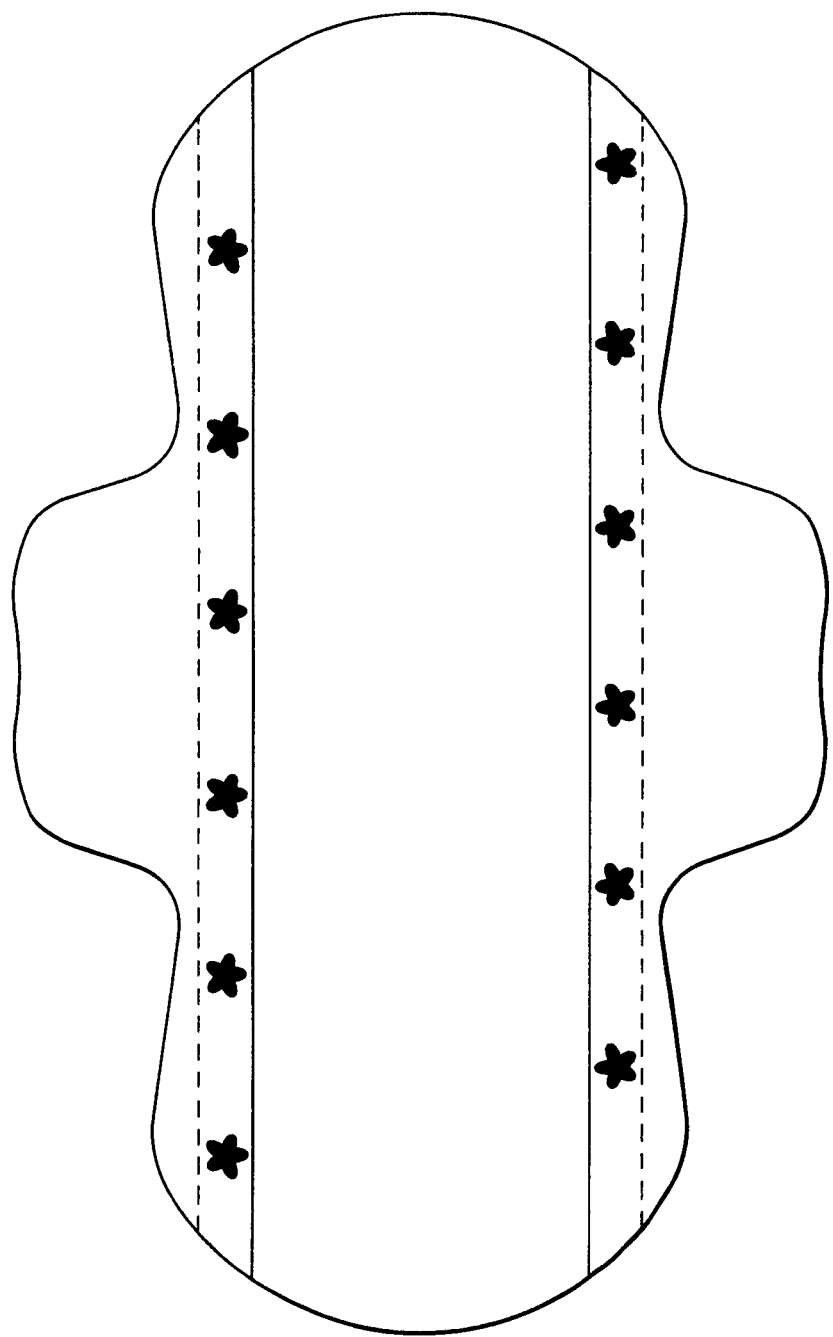
FIG. 4(a) is an example of solid pressed pattern embossing.
Figure 4B:
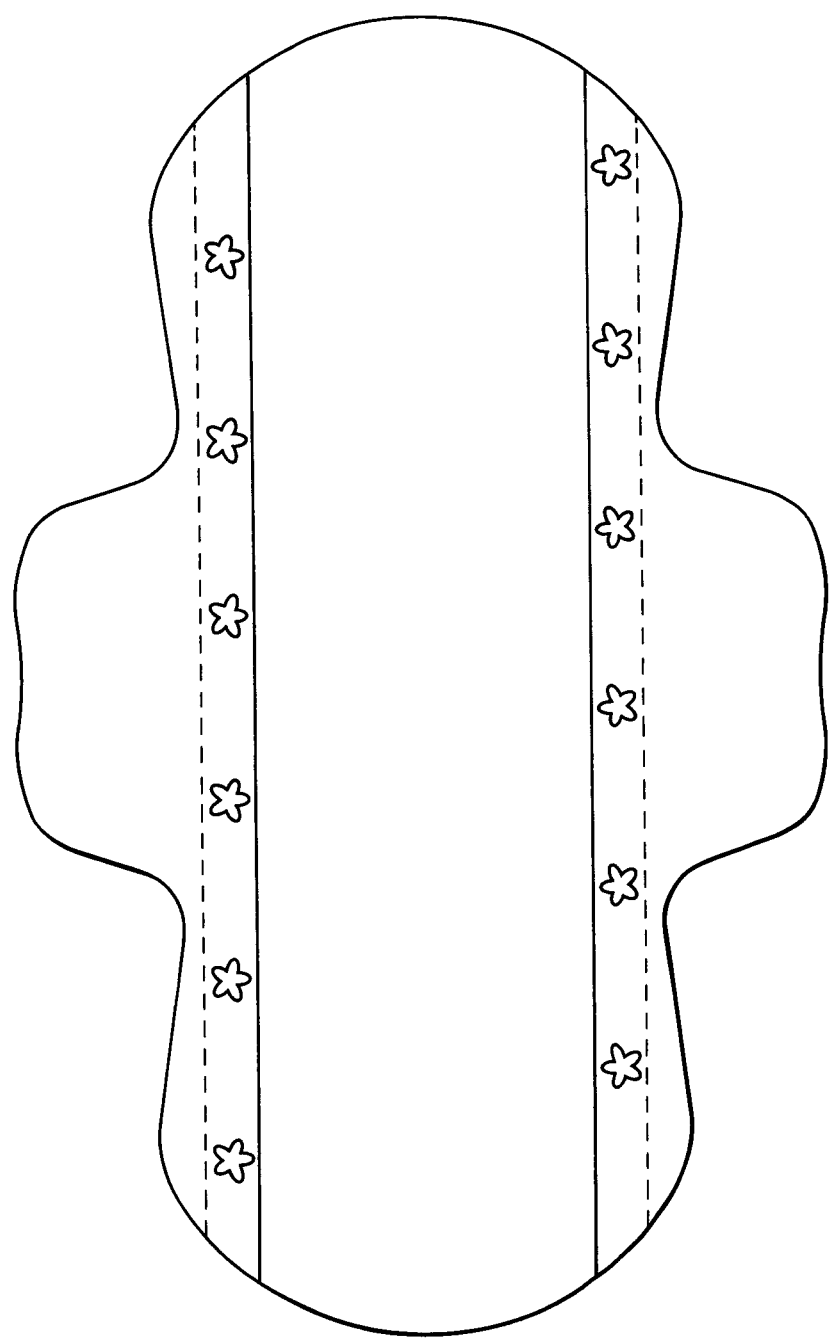
FIG. 4(b) is an example of fine line design embossing.
Figure 4C:
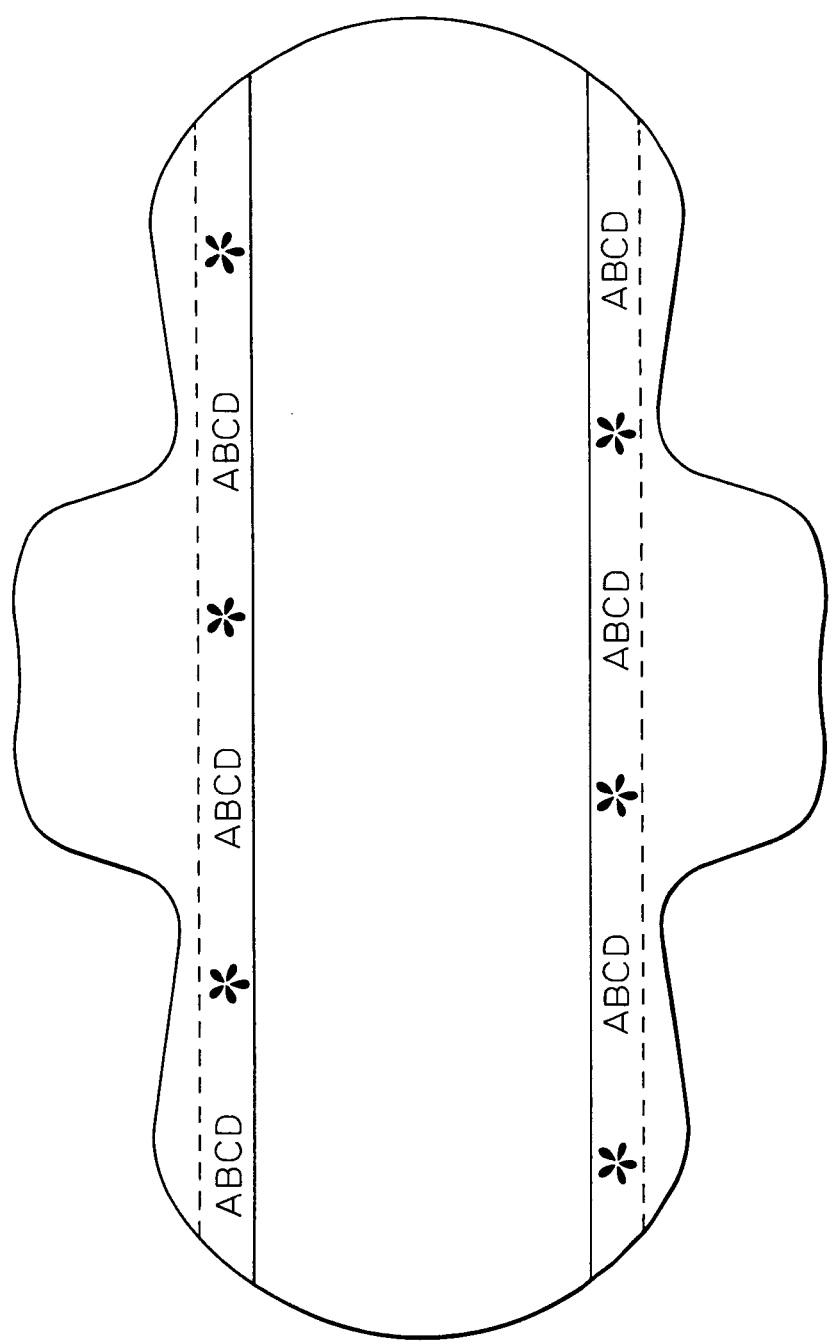
FIG. 4(c) is an example containing a message to the wearer.

FIG. 4 illustrates examples of the pattern. FIG. 4(a) is an example of solid pressed pattern embossing, FIG. 4(b) is an example of fine line design embossing, and FIG. 4(c) is an example containing a message to the wearer. How the pattern of the embossed part looks varies according to the coating method of the hot-melt resin. For example, the coating pattern of the hot-melt resin is changed in the emboss configuration of FIG. 4(a), FIG. 4(b) or FIG. 4(c), and the configuration of the coating pattern of the hot-melt resin is utilized as a design and combined with the design of embossing, whereby a new design can be visually recognized.

In the case of the solid coating pattern, the portion not coated with the hot-melt resin is not present and therefore, this coating pattern is suitable for both a solid pressed pattern illustrated in FIG. 4(a) and a design by a fine line illustrated in FIG. 4(b). This coating pattern can also cope with a design extending in the longitudinal direction of the product. In the case where a plurality of lines are formed in the longitudinal direction, whether the napkin should be replaced or not can be known by the range in which menstrual blood is diffused. An emboss for affixing side sheets to a liquid-permeable sheet so as to form pockets in the sides thereof can also be utilized as a design. A mark for the prevention of mixing up of the front and back may be attached by using a design showing the front and back clearly, such as an arrow, or a letter can be highlighted.

In the case of the coating pattern by a slot coater, a design requiring press-bonding of a relatively large area at a time is suitable. Such a design includes a sold pressed pattern and a pattern where characters, pictures or the like are obliquely disposed, though the area becomes small. The pattern can be shown, for example, to give the user an image of preventing leakage by highlighting the side or making the absorption center portion look wide. In this coating method, the hardness of the laminated product is reduced due to the presence of a non-coated portion. A design extending in the longitudinal direction of the product is not suitable, because the non-coated part is also extending in the longitudinal direction and it is difficult to emboss the design on the coated part.

In the case of the control seam coating, the coated part is wavy and therefore, the same designs as in the coating pattern by a slot coater are suitable.

In the case of the spiral coating, the resin is evenly coated similarly to the solid coating, and therefore the same designs as in the solid coating pattern are suitable. This coating is advantageous in that the sheet does not become hard, though a non-coated part is present and the color appears light compared with the solid coating.

In the case of the design coating by a roll coater, the roll coater can transfer a hot-melt resin having a design made by the coater itself, and therefore it can give a design may break the sheet if the design is made by embossing, such as a line shape extending in the longitudinal direction, or impart a three-dimensional appearance by combining a design by a roll coater with a design by embossing.

Regarding the method for providing a recess part, embossing is usually used, and heat embossing is preferable. As illustrated in FIG. 2, heat embossing is applied at the same time to the side sheet and the colored layer which differ in color tone from each other and in a recess part formed by embossing, the color of the colored layer becomes easily visible compared with the non-recess part, because the distance between the side sheet and the colored layer is small when seen from the side sheet side. In the case where the colored layer is a colored hot-melt resin, the hot-melt resin is melted due to heat during embossing and allowed to penetrate into the side sheet and be fixed by pressure, which is preferable. In the case of using a colored nonwoven fabric or film, unlike the case of using a hot-melt resin, the hot-melt resin is not melted due to heat and not allowed to penetrate into and be fixed to the side sheet, but by simultaneously embossing the side sheet and the colored layer, the side sheet having a certain degree of thickness is joined to the colored layer and the distance between them becomes small, and therefore the color tone of the colored layer in the recess part becomes easily visible compared with the non-recess part. As compared with the case of creating a pattern only by embossing without using coloration, embossing (temperature, pressure, clearance) can be made mild and this enables to prevent the embossed part and its periphery from becoming excessively hard, as a result, prickling or an uncomfortable feeling due to rubbing during wearing can be reduced and good skin touch can be obtained.

The embossing can be carried out using a commonly employed apparatus. For example, embossing is applied using an emboss roll having provided thereon protrusion parts in a desired pattern. Therefore, a plurality of members constituting the absorbent article may be joined and integrated at the same time as a pattern is provided. For example, simultaneously providing a plurality of recess parts in the side sheet, the side sheet, the colored layer and the liquid-permeable sheet may be joined and at the same time, the side sheet and the liquid-impermeable sheet may be bonded and the liquid-permeable sheet and the liquid-impermeable sheet may be bonded to each other. In the case where a colorant-containing hot-melt resin or hot-melt adhesive is used as the colored layer, embossing is preferably heat embossing and by the heat embossing, the side sheet and the liquid-permeable sheet can be adhered via the colored layer. In the case of using a side sheet coated entirely with a colorant-containing hot-melt resin or hot-melt adhesive or using a two-layer sheet where a side sheet and a colorant-containing hot-melt resin or hot-melt adhesive are stacked, by heat embossing, the side sheet and the liquid-permeable sheet can be adhered via the colored layer and at the same time, the side sheet and the liquid-impermeable sheet can be adhered.

EXAMPLES

Example 1

The sanitary napkin having a layer construction illustrated in the schematic cross-sectional view of FIG. 5 and having an appearance shape illustrated in the plan view of FIG. 1 was produced as follows.

A colored layer was coated on the edge of one side in the longitudinal direction of side sheets 5. For the colored layer, a material obtained by mixing 1 part by weight of Blue No. 404 as a colorant with 100 parts by weight of a hot-melt resin containing a styrene-butadiene-styrene block copolymer as the base polymer was used. As illustrated in FIG. 5, the portion of the side sheet, where the colored layer was provided, was turned back.

Figure 5:
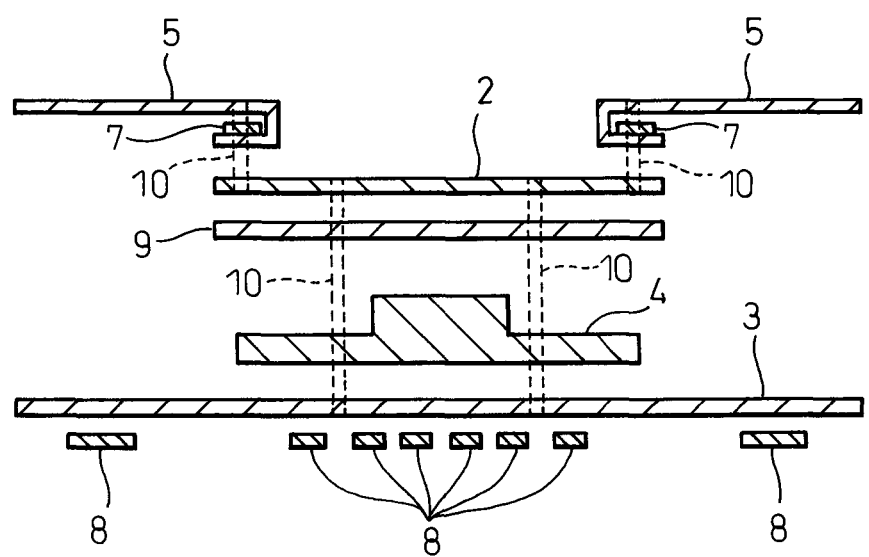
FIG. 5 is a schematic cross-sectional view showing the layer construction according to one embodiment of the absorbent article of the present invention.

A second liquid-permeable sheet 9, a liquid-permeable sheet 2 and side sheets 5 were stacked in the order illustrated in FIG. 5. One sheet of the side sheet 5 was then disposed on each of the right and left sides such that the turned-back portion was overlapped by a width of 10 mm with each of the right and left both edges of the liquid-permeable sheet 2. Incidentally, a hot-melt adhesive was coated on a necessary portion between respective members.

The stack obtained by stacking the members as above was heat-embossed by using a heat embossing roll to provide a recess part in the portion where the side sheet 5 and the liquid-permeable sheet 2 were overlapped, that is, the portion where the colored layer was present. Thereafter, an absorber 4 and a liquid-impermeable sheet 3 were stacked, and after integrating the stack, a slip stopper 8 was further coated on the surface of the liquid-impermeable sheet 3. The integrated stack was cut into the shape illustrated in FIG. 1 to obtain a sanitary napkin.

The obtained sanitary napkin was provided with a distinct pattern where the recess part was blue and the portion other than the recess part was white.

Example 2

Side sheets formed from various materials were evaluated for the thickness, the color difference (difference in the degree to which the color is seen through when the colored layer was stacked) and the entire light transmittance.

The materials prepared were an air-through nonwoven fabric (AT), a spunbonded fabric (PPSB), a film (material: polyethylene, thickness: about 30 μm), and a perforated film (PFW) (material: low-density polyethylene, thickness:about 0.45 mm, opening ratio: about 30%), and as for the air-through non-woven fabric, 5 kinds of fabrics were prepared, i.e., a fabric obtained by recovering a fiber having a fiber diameter of 2.2 dtex and a basis weight of 27 with aging to increase the bulk (AT1), a fabric having a fiber diameter of 1.6 dtex and a basis weight of 27 (AT2), a fabric having a fiber diameter of 1.6 dtex and a basis weight of 30 (AT3), a fabric having a fiber diameter of 2.2 dtex and a basis weight of 25 (AT4), and a fabric having a fiber diameter of 2.2 dtex and a basis weight of 30 (AT5).

The thickness was measured under a load of 3 g/cm$^2$ by using a thickness gauge manufactured by Peacock K.K.

As for the color difference, each material was stacked on a hot-melt resin (HMA) colored blue and the color difference was measured from the material side by using a colorimeter manufactured by Minolta Co., Ltd. At this time, the color difference base was that of the hot-melt resin alone. As the color difference value is larger, the difference in color tone between the side sheet and the colored layer is larger, i.e., the recess part can be more easily recognized as a pattern.

The total light transmittance TT (%) was measured by using a turbidimeter NDH-300A manufactured by Nippon Denshoku Industries Co., Ltd. The total light transmittance is the amount of light passing through the material, that is expressed by a ratio, and as this value is larger, the material transmits more light, i.e., the color of the colored layer can be more easily recognized with an eye when viewed from the side sheet.

The measurement results are shown in Table 1.

In Table 1, the ΔE value indicates the following.

From 0 to 0.5: Difference in color tone is scarcely recognized.

From 0.5 to 1.5: Difference in color tone is slightly recognized.

From 1.5 to 3.0: Difference in color tone is fairly recognized.

From 3.0 to 6.0: Difference in color tone is conspicuously recognized.

From 6.0 to 12: Difference in color tone is large.

12 or more: Difference in color tone is very large.

TABLE 1

| Material | Basis Weight | Thickness mm | Color Difference ΔE HMA 5 gsm | Color Difference ΔE HMA 10 gsm | Total Light Transmittance % |
|---|---|---|---|---|---|
| AT1 | 27 | 1.35 | 2.94 | 6.72 | 66.3 |
| AT2 | 27 | 0.35 | 3.84 | 7.14 | 67.2 |
| AT3 | 30 | 0.53 | 4.53 | 8.1 | 57.3 |
| AT4 | 25 | 0.4 | 4.02 | 7.75 | 62.1 |
| AT5 | 30 | 0.75 | 4.76 | 8.02 | 59.2 |
| PPSB | 25 | 0.15 | 1.26 | 2.76 | 85.8 |
| Film | 25 | 0.03 | 4.39 | 7.95 | 61.9 |
| PFW | 23.5 | 0.45 | 2.36 | 5.36 | 70.3 |

According to the results shown in Table 1, even with materials having the same basis weight, when the bulky air-through nonwoven fabric (AT4) and the spunbonded fabric (PPSB) reduced in the thickness by embossing are compared, in the case of laying a colored layer below the side sheet, the color difference greatly differs (the range where difference in color tone is fairly recognized) and the spunbonded fabric reduced in the thickness by embossing gives a low ΔE value and allows the color of the colored layer to be easily seen through. When air-through nonwoven fabrics having the same basis weight but differing in the thickness (AT3 and AT5) are compared, AT3 having a small thickness but having a small fiber diameter shows a tendency that the color of the colored layer becomes difficult to visually recognize.

The thickness in the level where the colored layer is not seen through the non-embossed part is, in the case of an air-through nonwoven fabric, preferably 0.2 mm or more, more preferably from 0.3 to 1.5 mm.

As for the total light transmittance, it is seen from the results of the color difference ΔE that PPSB having a total light transmittance of 86% showing transparency to color is not suitable as the side sheet. When 5 kinds of air-through nonwoven fabrics are compared, the total light transmittance is preferably 70% or less, more preferably 65% or less.

Example 3

An embossed sample was prepared using a colorant-mixed hot-melt resin, and how the color in the recess part looked was confirmed. A hot-melt resin using a styrene-butadiene-styrene block copolymer as the base polymer was used as the hot-melt resin, Blue No. 404 was used as the colorant, 5 kinds of colored hot-melt resins differing in the mixing ratio of the colorant (parts by weight of the colorant based on 100 parts by weight of the hot-melt resin) were prepared, and samples varied in color by changing the basis weight at coating were further prepared. An air-through nonwoven fabric (PET/PE, 27 gsm, titanium oxide was blended in a ratio of 2% based on the weight of the fiber) was stacked on the sample, and the stack was embossed. The color in the embossed part and the color in the non-embossed part were compared, and the color of the embossed part and the degree of see-through vision of the non-embossed part were evaluated.

A: Distinct difference in color and little see-through.
B: Difference in color is not so distinct.
C: Difference in color is scarcely recognized (the embossed part does not become dark, or the non-embossed part is excessively dark).

TABLE 2

Overall Evaluation of Contrast and See-Through Vision

|  |  | Mixing Ratio of Colorant (parts by weight) | | | | |
|---|---|---|---|---|---|---|
|  |  | 0.05 | 0.50 | 5 | 8 | 15 |
| Basis Weight at Coating | 3 gsm | C | B | B | A | C |
|  | 5 gsm | C | B | A | A | C |
|  | 10 gsm | C | A | A | B | C |
|  | 25 gsm | C | A | — | — | — |

In the overall evaluation of the color difference (contrast) between the embossed part and the non-embossed part and the degree of see-through vision of color of the colored layer from the side sheet in the non-embossed part, when the mixing ratio is 5% or less, the difference in color is not recognized unless the coating is performed at a high basis weight of 10 gsm or more. However, coating at a high basis weight causes a problem that, for example, the hot-melt resin bleeds out when folding the material by a guide plate generally called a "sailor" and therefore accumulates on the guide plate or the hot-melt resin is melted due to heat when applying embossing, and thus bleeds out due to pressure, causing the material to twine around the emboss roll. Accordingly, the preferred range for the mixing ratio of the colorant, where coating can be performed at 10 gsm or less and the embossed part can be clearly recognized owing to the contrast of color tone, is 0.1% or more, preferably 0.1 to 10%.

INDUSTRIAL APPLICABILITY

The absorbent article of the present invention can be used as a sanitary napkin, a diaper and the like. The absorbent article of the present invention can provide an aesthetic value by virtue of a colored pattern applied thereto. In particular, in the case where the absorbent article is a sanitary napkin, even when menstrual blood is attached to the side sheet, the pattern provides an effect of masking the menstrual blood and in turn, alleviating depression during menstruation. Furthermore, a colored pattern is provided on both sides and gives an indication of positioning relative to underwear and therefore, the sanitary napkin can be easily fitted.

The invention claimed is:

1. An absorbent article, comprising;
a liquid-permeable sheet,
a liquid-impermeable sheet,
an absorber sandwiched between said liquid-permeable sheet and said liquid-impermeable sheet,
side sheets joined to said liquid-permeable sheet on transversely opposite sides of said liquid-permeable sheet, respectively, and
a colored layer positioned on said liquid-permeable sheet at a user-facing side,
wherein
at least one of the side sheets includes a plurality of recess parts,
the colored layer is provided at at least one of said recess parts of the side sheet and is arranged between said side sheet and said liquid-permeable sheet,
the liquid-permeable sheet extends transversely outwardly from each side edge of the absorber, and
said recess parts appear in a color different from a portion of the side sheet outside the recess parts.

2. The absorbent article according to claim 1, wherein said recess parts comprise embossed parts.

3. The absorbent article according to claim 1, wherein a light transmittance of said side sheet is 70% or less.

4. The absorbent article according to claim 1, wherein a thickness of said side sheet is from 0.2 to 1.5 mm under a load of 3 g/cm$^2$.

5. The absorbent article according to claim 1, wherein said colored layer comprises a hot-melt resin containing a colorant.

6. The absorbent article according to claim 5, wherein said colored layer contains from 0.1 to 10 parts by weight of the colorant based on 100 parts by weight of said hot-melt resin.

7. The absorbent article according to claim 1, wherein the colored layer is directly sandwiched between the liquid-permeable sheet and the side sheet.

8. The absorbent article according to claim 1, wherein the colored layer is directly provided on an uppermost face of the liquid-permeable sheet.

9. The absorbent article according to claim 8, wherein the side sheet is folded back to define a folded portion, and the colored layer is between the folded portion and the liquid-permeable sheet.

10. The absorbent article according to claim 1, wherein the side sheet is folded back to define a folded portion, and the colored layer is positioned adjacent to the folded portion in a transverse direction of the liquid-permeable sheet.

11. An absorbent article, comprising:
a liquid-permeable sheet,
a liquid-impermeable sheet,
an absorber sandwiched between said liquid-permeable sheet and said liquid-impermeable sheet,
side sheets joined to said liquid-permeable sheet on transversely opposite sides of said liquid-permeable sheet, respectively, and
a colored layer directly positioned on said liquid-permeable sheet,
wherein
at least one of the side sheets includes a plurality of recess parts,
the colored layer is provided at at least one of said recess parts of the side sheet and is arranged between said side sheet and said liquid-permeable sheet, and
said recess parts appear in a color different from a portion of the side sheet outside the recess parts.

12. A method of producing an absorbent article which comprises a liquid-permeable sheet, a liquid-impermeable sheet, an absorber sandwiched between said liquid-permeable sheet and said liquid-impermeable sheet, side sheets joined to said liquid-permeable sheet on transversely opposite sides of said liquid-permeable sheet, respectively, and a colored layer provided between said liquid-permeable sheet and at least one of said side sheets, wherein the at least one of the side sheets is provided with a plurality of recess parts appearing in a color different from a portion of the side sheet outside the recess parts,
the method comprising;
stacking a liquid-permeable sheet, a colored layer and a side sheet in the recited order; and
applying embossing to a region of the side sheet where the colored layer is present, thereby providing a plurality of recess parts in the side sheet, wherein the colored layer is directly positioned on said liquid-permeable sheet.

13. The method according to claim 12, wherein the colored layer is directly sandwiched between the liquid-permeable sheet and the side sheet.

14. The method according to claim 12, wherein the colored layer is directly provided on an uppermost face of the liquid-permeable sheet.

15. The method according to claim 14, wherein the side sheet is folded back to define a folded portion, and the colored layer is between the folded portion and the liquid-permeable sheet.

16. The method according to claim 12, wherein the side sheet is folded back to define a folded portion, and the colored layer is positioned adjacent to the folded portion in a transverse direction of the liquid-permeable sheet.

* * * * *